United States Patent [19]
Blomquist

[11] Patent Number: 5,810,771
[45] Date of Patent: Sep. 22, 1998

[54] SYSTEMS AND METHODS FOR AUTOMATED TESTING OF MEDICAL EQUIPMENT

[75] Inventor: Michael L. Blomquist, Coon Rapids, Minn.

[73] Assignee: SIMS Deltec, Inc., St. Paul, Minn.

[21] Appl. No.: 934,875

[22] Filed: Sep. 22, 1997

Related U.S. Application Data

[62] Division of Ser. No. 206,737, Mar. 7, 1994, Pat. No. 5,669,877.

[51] Int. Cl.$^6$ .................................................. A61M 31/00
[52] U.S. Cl. ............................................. 604/65; 604/30
[58] Field of Search ............................... 604/65–67, 246, 604/30, 31; 128/DIG. 12, DIG. 13

[56] References Cited

U.S. PATENT DOCUMENTS

| | | |
|---|---|---|
| 4,137,913 | 2/1979 | Georgi . |
| 4,559,038 | 12/1985 | Berg et al. . |
| 4,565,542 | 1/1986 | Berg . |
| 4,623,331 | 11/1986 | Cewers et al. . |
| 4,650,469 | 3/1987 | Berg et al. . |
| 4,808,161 | 2/1989 | Kamen . |
| 4,869,722 | 9/1989 | Heyman . |
| 5,006,997 | 4/1991 | Reich . |
| 5,087,245 | 2/1992 | Doan . |
| 5,098,409 | 3/1992 | Stock . |
| 5,100,380 | 3/1992 | Epstein et al. . |
| 5,140,862 | 8/1992 | Pappalardo . |
| 5,181,910 | 1/1993 | Scanlon . |
| 5,190,522 | 3/1993 | Wojcicki et al. . |
| 5,354,273 | 10/1994 | Hagen . |
| 5,383,855 | 1/1995 | Nicholson et al. . |

*Primary Examiner*—Manuel Mendez
*Attorney, Agent, or Firm*—Merchant, Gould, Smith, Edell, Welter & Schmidt, P.a.

[57] ABSTRACT

A closed-loop system automates the testing of medical devices. The system includes a medical device, a testing device, and a computer. The medical device has a tube for transporting a fluid and is programmed to perform various tests. The testing device is connected to the tube of the medical device to measure various parameters related to the tests conducted by medical device. The computer is electrically connected to both the medical device and the testing device for substantially automating the testing of the medical device.

1 Claim, 10 Drawing Sheets

SYSTEMS AND METHODS FOR AUTOMATED TESTING OF MEDICAL EQUIPMENT

"This is a Divisional of application Ser. No. 08/206,737, filed Mar. 7, 1994, now U.S. Pat. No. 5,669,877 which application(s) are incorporated herein by reference.

FIELD OF THE INVENTION

The present invention relates to systems and methods for automated testing of medical equipment, such as an infusion pump.

BACKGROUND OF THE INVENTION

In the health care industry, the provision and maintenance of safe and accurate medical equipment is of the utmost importance. A failure or defect in a medical device can prevent the patient from receiving an accurate diagnosis or proper treatment. In some cases, such failures or defects may cause serious health consequences to the patient, including death. In the case of an infusion pump which delivers drugs or other fluid to the patient at predetermined times, a properly functioning pump can be critical for delivering the proper therapy to the patient.

As a result, hospitals and caregivers have developed detailed testing procedures to ensure the safety and integrity of such equipment. The frequency and extent of such tests depends on the type of equipment being tested. The equipment may be evaluated both before it is put into use, and at specified intervals throughout the lifetime of the equipment. In some instances, it may be desireable or necessary to test the equipment after each use.

The need for testing has become even more immediate due to organizations like the Joint Commission on Accreditation of Health Care Organizations ("JCAHO"). JCAHO accredits health care organizations that provide safe and effective services. Hospitals receiving such accreditation not only gain the trust and respect of the community to which they serve, but often receive breaks or discounts from their insurance carriers. In today's market, where competition between health care providers is fierce, and where such providers are constantly struggling to reduce operating costs, such advantages are invaluable.

Many existing testing techniques, however, involve operations which must be performed manually. In the case of infusion devices, typical tests include flow rate and occlusion, or pressure, tests. Currently, such tests are performed using calibrated burettes, stop watches, and pressure measuring devices. As a result, testing all of the equipment in even a small sized facility on a frequent basis can be very time consuming. In the case of large hospitals, manual testing of all of their equipment may be impossible.

Besides being time consuming, manual testing can also be inaccurate. Errors may be introduced by the test operator during the testing phase due to the wide variances in drop sizes, drop detector malfunction, lack of access to drip chambers, improperly primed tubing, and/or instantaneous flow/volume boluses. Errors can also be introduced in the testing phase due to user misprogramming, or in the reporting phase as a result of the test operator entering incorrect test results. Consequently, consistency and accuracy in both the testing and record-keeping procedures cannot be ensured.

Moreover, since testing and other related information is manually recorded, it is only accessible to the person having physical possession of such records. While copies can be made and distributed to the appropriate persons, they cannot be automatically updated as new tests are performed. Rather, a new updated record must be completed and new copies must be made and distributed. As a result, this procedure not only increases the administrative costs associated with maintaining such records, but also increases the risk that someone may have information which is not current. Device tracking is also difficult in these settings.

In addition, manual testing requires the maintenance of considerably sized and highly trained staff. The staff must be trained not only on how to conduct the test, but also on how to operate the piece of equipment being tested. With medical equipment becoming increasingly sophisticated and complex, the level of such training may be extensive. The cost of maintaining and training such a staff, however, is often prohibitive. As a result, health care providers often send the testing out to third-party testing organizations. These organizations, however, are typically for-profit organizations. Consequently, this alternative for testing can prove just as costly as testing the devices in-house. Additionally, since the testing is done out-of-house, the equipment being tested becomes temporarily out of service. Thus, hospitals must maintain an increased inventory in order to maintain a sufficient quantity of medical devices on hand at all times, thereby increasing the cost of this alternative method of testing.

Some attempts have been made to develop products that automate the testing process. An example of a company that distributes a line of such testing products is Bio-Tek Industries, Inc. One testing scenario involves the medical device being hooked up to the appropriate testing device. The testing device performs the appropriate tests on the medical device and records the results. One major setback with this configuration, however, is that many of the testing steps must still be manually performed.

Accordingly, a need has arisen among health care organizations to create more automated systems and methods for testing medical equipment in a simple, accurate, fast, and cost-effective manner.

SUMMARY OF THE INVENTION

The present invention fulfills the need for simple, accurate, fast, and cost-effective testing of medical equipment. More particularly, one aspect of the invention relates to a closed loop medical equipment testing system for automated testing of medical equipment. The system includes a medical device having a tube for transporting a fluid, a testing device connected to the tube of the medical device for testing the medical device, and a computer electrically connected to the medical device and to the testing device for controlling the operation of the medical device and the testing device during testing.

The medical device includes a pump mechanism and a control system for pumping fluid through the tube. Memory in the control system stores programs to permit communication between the medical device and the computer, and to permit the running of one or more test procedures to test the operation and integrity of the medical device.

The testing device includes a flow rate tester, a pressure tester, or preferably both. The flow rate tester tests the accuracy of the flow rate of the medical device, while the pressure tester tests the accuracy of the medical device's response to an occlusion in the fluid transporting tube.

The medical device further includes input structure for allowing an operator to input information to the medical device. The medical device also includes sensors, switches or other devices for sensing a variety of conditions.

The medical device is preferably programmed to conduct a self-test, a maintenance test, or preferably both. The computer provides the appropriate commands to the medical device to initiate such tests. The self-test tests the diagnostics of the medical device. The maintenance test tests the structural integrity of the medical device. The medical device is also preferably programmed to allow for operator interaction with the computer, the medical device, and the testing device. In particular, such interaction involves providing the operator with a plurality of instructions for testing the accuracy of the sensors and for performing the maintenance test. The medical device preferably includes a memory for storing the results of all such tests and any related information.

The computer preferably includes a display for displaying the testing instructions, as well for displaying the results of the flow rate test, the pressure test, the self-test, and the maintenance test.

The system further includes a printer connected to the computer for printing out the results of the flow rate test, the pressure test, the self-test, and the maintenance test.

A further aspect of the invention relates to a closed loop system for automated testing of medical equipment which includes a pump, a testing device, and a computer, wherein a first connector electrically connects the computer to the pump, and a second connector electrically connects the computer to the testing device.

The pump preferably includes a fluid outlet tube for delivering a fluid, and a pump mechanism for pumping fluid through the fluid outlet tube. The pump also includes a processor, and a communications port interconnected to the processor for providing the computer with access to the processor.

The testing device includes a fluid inlet connected to the fluid outlet tube of the medical device, and a fluid outlet in fluid communication with the fluid inlet. The testing device also includes a flow rate testing system and a pressure testing system between the fluid inlet and the fluid outlet for testing the flow rate and the pressure of the medical device, respectively. The testing device further includes a processor and a communications port interconnected to the processor for providing the computer with access to the processor of the testing device.

The computer includes a processor. A display is interconnected to the processor of the computer for displaying information to an operator. A keyboard is also interconnected to the processor of the computer for allowing the operator to input information to the computer. The computer also includes a first communications port and a second communications port interconnected to the processor of the computer. The first electrical connector of the computer connects the first communications port of the computer to the communications port of the pump. The second electrical connector of the computer also connects the second communications port of the computer to the communications port of the testing device.

Another aspect of the invention relates to a method of automating the testing of a medical device. The method includes the steps of electrically connecting the computer to both the medical device and the testing device, and connecting the tube of the medical device to the testing device.

The method includes the steps of running a flow rate test, a pressure test, or preferably both, with the testing device. The testing device sends a signal to the computer representative of the flow rate and/or pressure measured. The medical device sends a signal to the computer representative of the flow rate and/or pressure of the medical device. The computer then determines the accuracy of the flow rate and/or pressure of the medical device. The method also includes the steps of running a self-test, a maintenance test, or preferably both, on the medical device, and sending a signal from the medical device to the computer representative of the results of such tests. The method also preferably includes the steps of printing the results of the flow rate test, the pressure test, the self-test, and the maintenance test.

The method preferably includes the steps of displaying a testing instruction on the display of the computer, and sending a signal from the medical device to the computer representative of the instruction performed.

BRIEF DESCRIPTION OF THE DRAWINGS

In the drawings where like numerals refer to like features throughout the several views.

DETAILED DESCRIPTION OF THE PREFERRED EMBODIMENT

The present invention concerns a system for automated testing of a pump, which includes a computer electrically connected to both a testing device and a pump. The pump is connected to the testing device by the pump's fluid tube so that a closed loop configuration is obtained. The medical device is programmed to conduct a variety of tests upon receiving commands from the computer. The testing device provides for measurement of various parameters during the performance of these tests, such as flow rate and pressure. The medical device and/or computer may be programmed to store the test results. By providing a central place for storing such information, not only can each pump be tracked as it moves from location to location, information relating to that pump can be automatically updated. With such a configuration, the testing of the pump is substantially automated.

Figure 1:
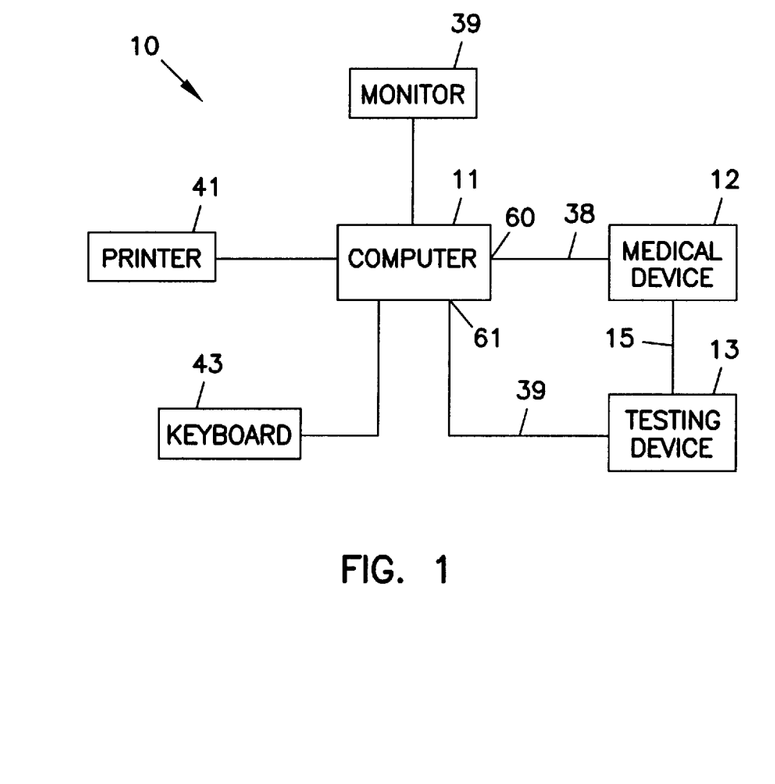
FIG. 1 is a schematic diagram of an automated testing system according to one embodiment of the present invention.

Referring now to FIG. 1, a system 10 for testing a medical device 12 is shown. The system 10 includes three major components: a computer 11, a medical device 12, and a testing device 13. For illustrative purposes only, medical device 12 is a drug delivery device, such as an infusion pump, having a fluid communication structure, such as a tube 15, for delivering a drug or other fluid to a patient at a selected flow rate. Examples of infusion pumps are shown and described in U.S. Pat. Nos. 4,559,038; 4,565,542; 4,650,469; and 4,731,058, the disclosures of which are incorporated herein by reference. Each of the components of system 10 will now be described in further detail below.

Figure 2:
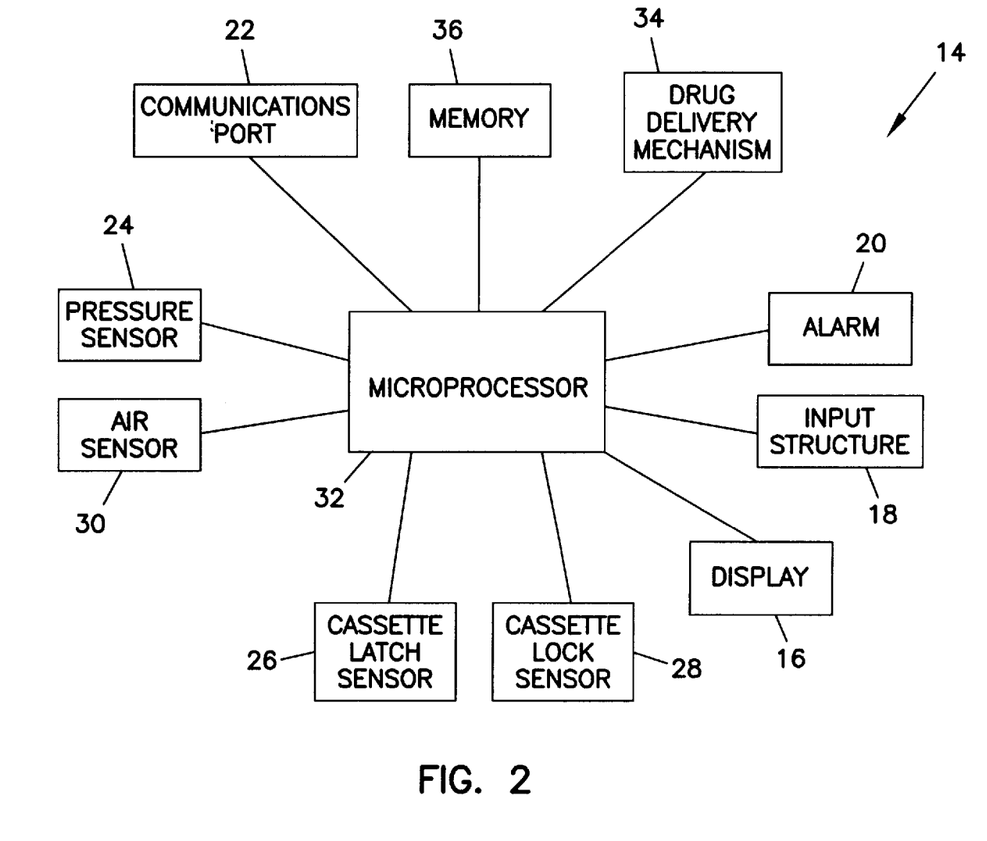
FIG. 2 shows a block diagram of a control system for the medical device shown in FIG. 1.

Major components of medical device 12 are illustrated in FIG. 2. Medical device 12 includes a control system 14 for controlling the operation of medical device 12. Control system 14 includes a microprocessor 32 and a memory 36 programmable with selected functions for controlling operation of a drug delivering mechanism 34, including, for example, a motor and motor control circuitry (not shown) and the other features of medical device 12. Medical device 12 may also be designed and configured to accept a plurality of memory modules or cassettes (not shown) containing information defining specific operational characteristics. Specifically, memory 36 stores various programs and data related to the operation of medical device 12. Memory 36 is coupled to microprocessor 32, which in turn runs the desired operating programs which control operation of drug delivery mechanism 34. Stored in memory 36 is the program to permit communication with computer 11, and the program to run one or more tests involving the operation of components of medical device 12.

Access to microprocessor 32 is provided through communications port 22. Communications port 22 is preferably a standard RS232 communications port. Information programmed into memory 36 instructs information to be transmitted or received via communications port 22. This feature allows information being received via communications port 22 from computer 11 to control medical device 12. This feature also allows for the downloading of any or all information from memory 36 to computer 11. This information can then either be displayed on display 16, printed out via printer 41, or stored for future recall.

Medical device 12 may also include operator input structure 18 for providing information to microprocessor 32. One such structure is a keypad or keyboard which permits an operator to communicate with medical device 12. The keyboard includes at least one key for pressing by the operator, the key having at least one function. When pressed, the key sends a signal to microprocessor 32 indicative of the key being pressed. Microprocessor 32 responds to the signal received in the desired manner. Other such input structures may include knobs, buttons, or other like structures for performing pump functions, such as starting, stopping, and priming medical device 12.

Medical device 12 may also include a display 16, such as a liquid crystal display ("LCD"). Display signals sent from microprocessor 32 permit display of information related to the operation of medical device 12.

Medical device 12 may also be provided with a variety of sensors, switches, or other devices (hereinafter "sensors"). The type of sensors provided depends on the type of medical device and its intended usage. Examples of such sensors may include a pressure sensor 24 for detecting occlusions in tube 15, a cassette latch sensor 26 for indicating whether the cassette's latch is open or closed, a cassette lock sensor 28 for indicating whether the latch is locked, and an air sensor 30 for detecting air in tube 15. The sensors typically send a suitable electrical signal to microprocessor 32 indicative of the condition sensed. Microprocessor 32 is appropriately programmed to receive and process such signals.

In addition, medical device 12 may also be equipped with visual and/or audible alarms 20 which are activated by the sensing of one of the conditions mentioned above. Alarms 20 may be activated as a result of other triggering events, such as error conditions with respect to the power supply or pump hardware. Alarm signals sent from microprocessor 32 permit activation of alarms 20.

As shown in FIG. 1, medical device 12 is connected to testing device 13 via tube 15, such as a flexible, compressible tube made of polymeric material. In the case of a peristaltic pump, tube engaging members of drug delivery mechanism 34 engage tube 15 to pump fluid during use.

Figure 3:
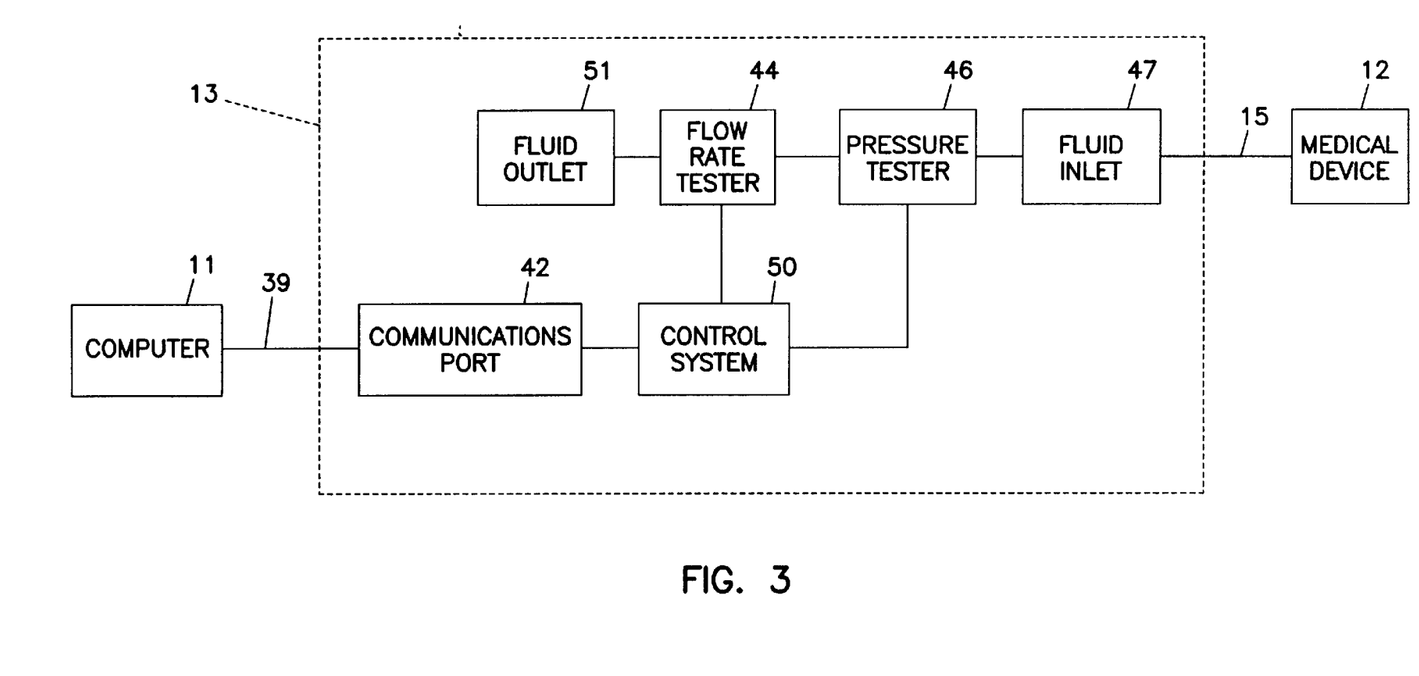
FIG. 3 shows a block diagram of one embodiment of the testing device shown in FIG. 1.

Major components of testing device 13 are illustrated in FIG. 3. Testing device 13 is connected to tube 15 of medical device 12 via fluid inlet 47. Testing device 13 includes a flow rate tester 44 and a pressure tester 46. Flow rate tester 44 tests the accuracy of the flow rate of a drug being delivered by medical device 12. Pressure tester 46 tests the accuracy of medical device's pressure sensor 24 and/or alarms 20 in response to an occlusion in tube 15. Pressure tester 46 measures the pressure generated over time until medical device 12 stops, alarm 20 sounds, or medical device 12 reaches a certain predetermined test pressure set by computer 11. Computer 11 then compares the pressure measured by testing device 13 to the pressure of medical device 12 once alarm 20 sounds or the predetermined test pressure has been reached to determine pressure accuracy. In a preferred embodiment, pressure tester 46 can test at multiple test pressures, such as a range from a low pressure to a high pressure. Testing device 13 is equipped with a fluid outlet 51 for releasing the fluid which runs through testing device 13 during the flow rate and pressure tests.

Access to testing device 13 is provided through communications port 42. Preferably, communications port 42 is a standard RS232 communications port. This feature allows information being received via communications port 42 from computer 11 to control testing device 13.

A control system 50 is provided for controlling operation of flow rate tester 44 and pressure tester 46, as well as for controlling communication between testing device 13 and computer 11. Control system 50 includes a microprocessor and associated memory for controlling operation of testing device 13. Testing device 13 may also include an optional display, for displaying information, such as that related to the tests conducted by flow rate tester 44 and pressure tester 46.

One preferred testing device which may be used in system 10 is an Infusion Device Analyzer (IDA) made by Ultramedic, Ltd. of Liverpool, England, and distributed by Bio-Tek Instrument, Inc. of Winooski, Vt. The IDA tests a variety of drug delivery devices, such as infusion pumps.

As is further shown in FIG. 1, both medical device 12 and testing device 13 are interconnected to computer 11 via communications links 38 and 39 to form a closed loop testing system. Preferably, computer 11 is a personal computer and communications links 38 and 39 are RS232 cables. Communication links 38 and 39 connect to computer 11 via communications ports 60 and 61, respectively.

Computer 11 further includes a monitor 39 for displaying information related to the operation of system 10, such as test instructions, test results, etc. Such information may also be delivered via hard copy printout to printer 41 attached to computer 11. Computer 11 may also include a keyboard 43 for inputting information into computer 11. Data may also be input into computer 11 via disk, tape, or card reader.

Computer 11 preferably includes a control system for controlling operation of the computer. The control system includes at least a microprocessor and an associated memory with selected functions for controlling operation of the computer. In particular, the memory stores various programs and data needed to run the tests performed on medical device 12, such as those performed by flow rate tester 44 and pressure tester 46. Such programs and data may also be stored via disks which may be inserted into computer 11.

Information programmed into computer 11 permits an operator to communicate over communications links 38 and 39 with both medical device 12 and testing device 13, respectively. Via communications link 39, computer 11 instructs testing device 13 to measure the flow rate and/or pressure and requests the results of such measurements. With the addition of communications link 38, however, many of the steps performed on medical device 12 by flow rate tester 44 and pressure tester 46, which would otherwise have to be performed manually, are now automated.

Communications link 38 also allows for the automation of tests other than the flow rate and pressure tests previously mentioned herein. In particular, via communications link 38, computer 11 can instruct medical device 12 to pump fluid for a flow rate test or a pressure test, or to perform internal tests, such as a self-test 190 (see FIG. 5) and a maintenance test 550 (see FIGS. 8A and 8B). Self-test 190 tests the diagnostics of the medical device, such as memory 36 and motor control circuitry (not shown). Maintenance test 550 tests whether operator input structure 18, sensors, and/or alarms 20 of medical device 12 is operating properly. It also tests the structural integrity of medical device 12, including such items as the frame of the device, any power cord, the cassette latch/lock, and any knobs or buttons. As a result of this closed loop configuration, the testing of medical device 12 is substantially automated.

Figure 4:
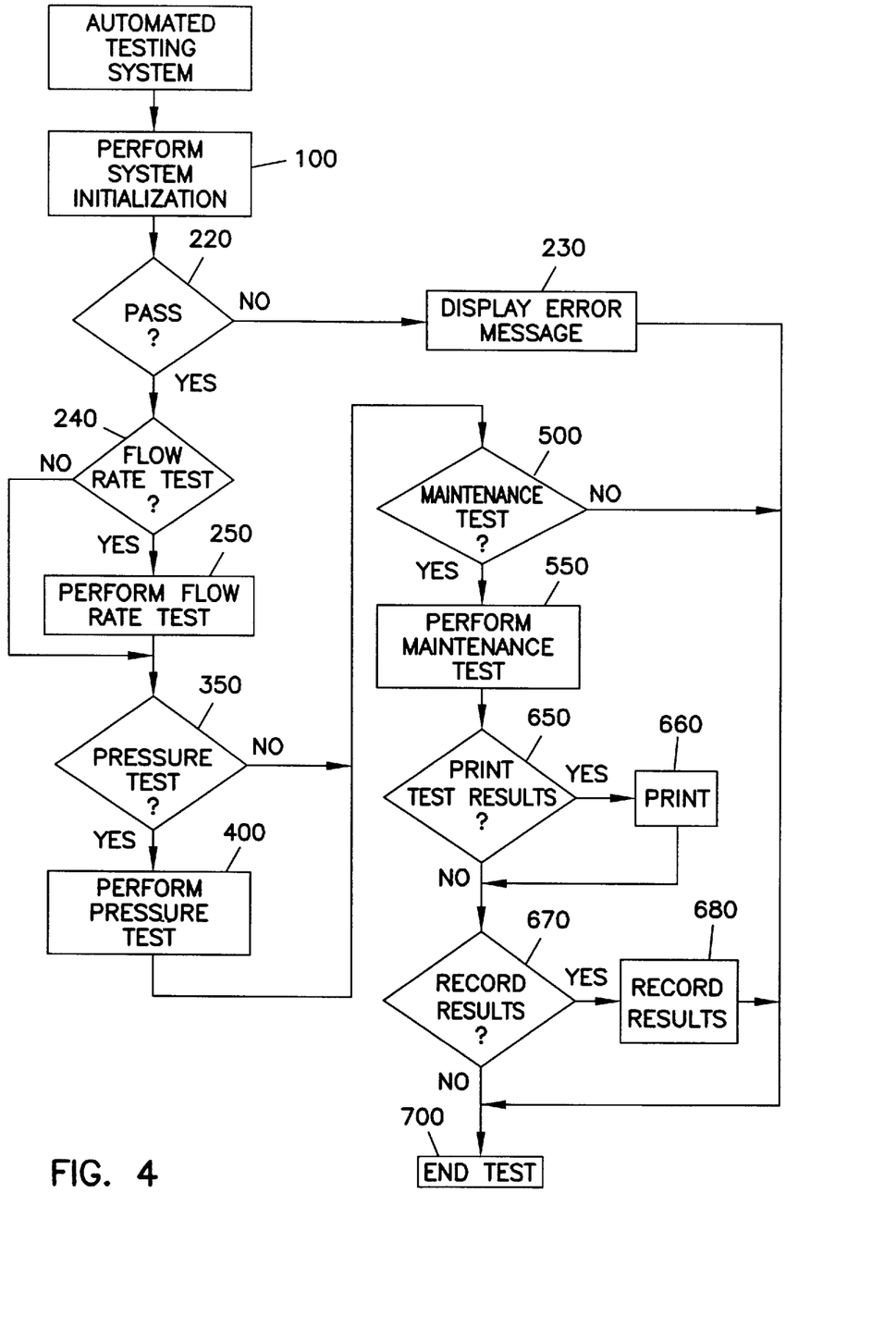
FIG. 4 is a flow chart representation of the preferred steps taken during the testing of the medical device shown in FIG. 1.

Referring now to FIG. 4, a flow chart is shown illustrating one preferred operational sequence of testing system 10 as shown in FIG. 1 for a drug pump 12. The sequence assumes that all components are connected. Alternatively, computer 11 could instruct the user via monitor 39 to verify the connections between components before beginning the testing process. Once all the components of system 10 are properly connected, system 10 may begin testing.

Specifically, at 100, the system is initialized. At 220, a check is made whether pump 12 successfully completed system initialization 100. If not, at 230, a message is displayed on monitor 39 of computer 11 detailing the error and requesting service, and at 700, the testing procedures are ended. If system initialization 100 is successful, system 10 then conducts a series of tests, such as those performed by flow rate tester 44 and pressure tester 46, as well as maintenance test 550. The list of tests mentioned above, however, is not exclusive. Depending on the medical device being tested, cost constraints, and/or the testing history of the device, more or fewer tests may be performed. Moreover, as those skilled in the art can appreciate, the order in which the tests are performed is not critical.

At 240, a check is made to determine whether the flow rate of pump 12 should be tested. If so, at 250, flow rate tester 44 performs a flow rate test. If not, at 350, a check is made to determine whether the pressure of pump 12 should be tested. If so, at 400, pressure tester 46 performs a pressure test. If not, at 500, a check is made to determine whether a maintenance test should be performed. If so, at 550, a maintenance test is performed. If not, at 650, after all desired tests have been performed, a check is made whether test results should be printed. If so, at 660, a signal is sent to printer 41 to start printing the test results. If not, at 670, a check is made whether the test results should be recorded. If so, at 680, computer 11 records the results. If not, at 700, the testing process is ended.

The flow charts of FIG. 5 through 8 show more specific operational sequences of each of the tests identified in FIG. 4. The flow charts represent the communication between computer 11 and both pump 12 and testing device 13, as well as any operator interaction with computer 11, pump 12 and testing device 13.

Figure 5:
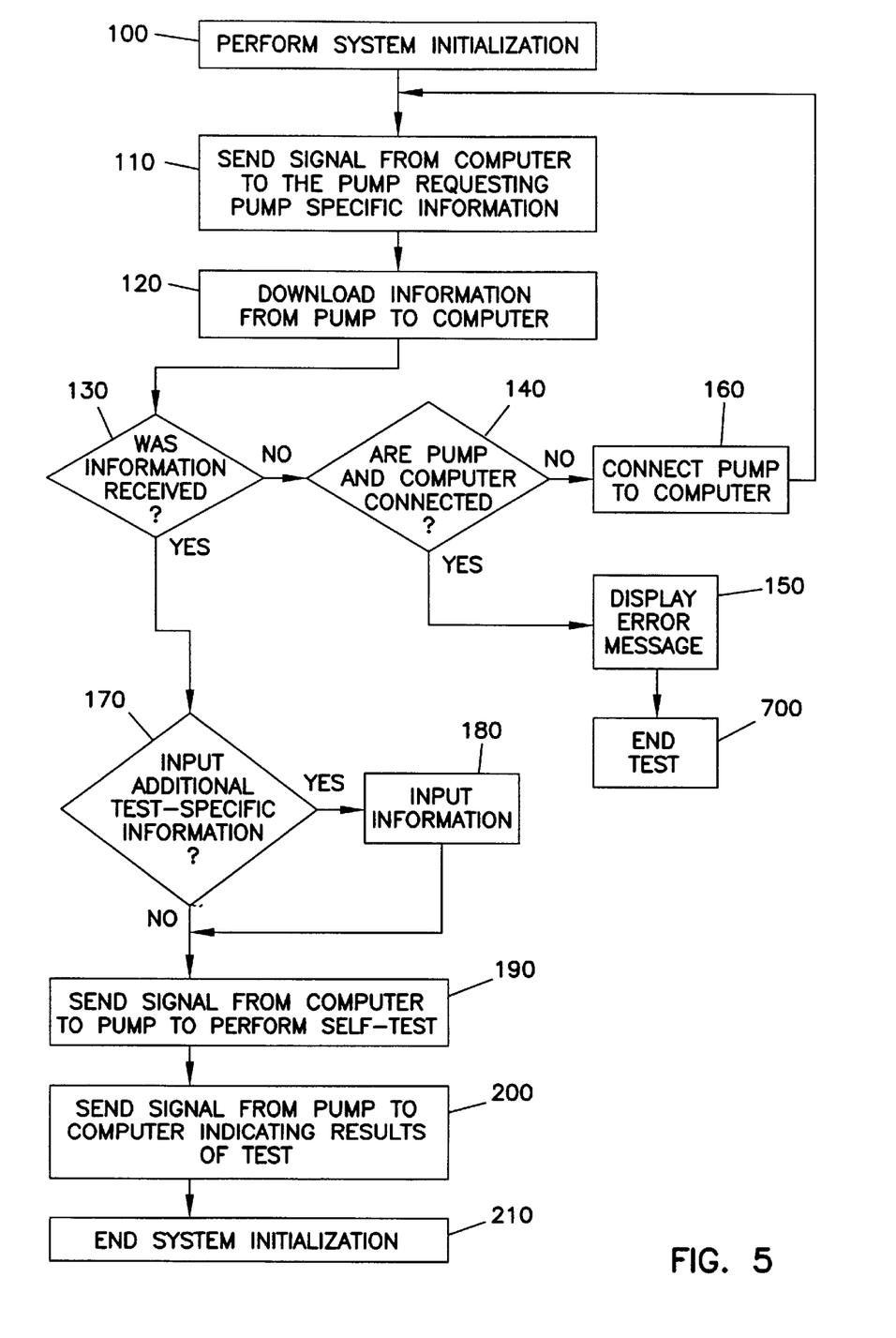
FIG. 5 is a flow chart representation of the preferred steps taken during system initialization as identified in the flow chart of FIG. 4.

Referring now to FIG. 5 which illustrates a flow chart representation of the steps in a preferred system initialization 100, at 110, computer 11 sends a signal to pump 12 requesting pump specific information from pump 12. Such information may include the device type (syringe, peristaltic, volumetric, etc.), the device's serial number, the manufacturer of the device, and the date of the last test. In the case where pump 12 is dedicated to a patient for extended periods of time, such information may also include the patient's name and address, as well as the name and address of the referring physician. At 120, pump 12 downloads the requested information to computer 11. Such information is useful for device tracking with computer 11.

At 130, a check is made to determine whether computer 11 received the information from the pump. If not, at 140, a further check is made to determine whether pump 12 and computer 11 are in fact connected. If so, at 150, a message is displayed on monitor 39 detailing the error and requesting service, and at 700, the testing process is ended. If not, at 160, computer 11 instructs the operator to connect pump 12 to computer 11, and then repeats steps 110 through 130.

If the information is received by computer 11, at 170, the operator has the option of including additional information, such as the operator's name, and the date and location of the test. If the operator chooses to add information, at 180, he or she may input the information into computer 11 via keyboard 43. If no additional information is added, at 190, computer 11 sends a signal to pump 12 to begin self-test 190. At 200, pump 12 sends a signal back to computer 11 representative of the results of self-test 190. At 210, system initialization 100 is complete.

Figure 6A:
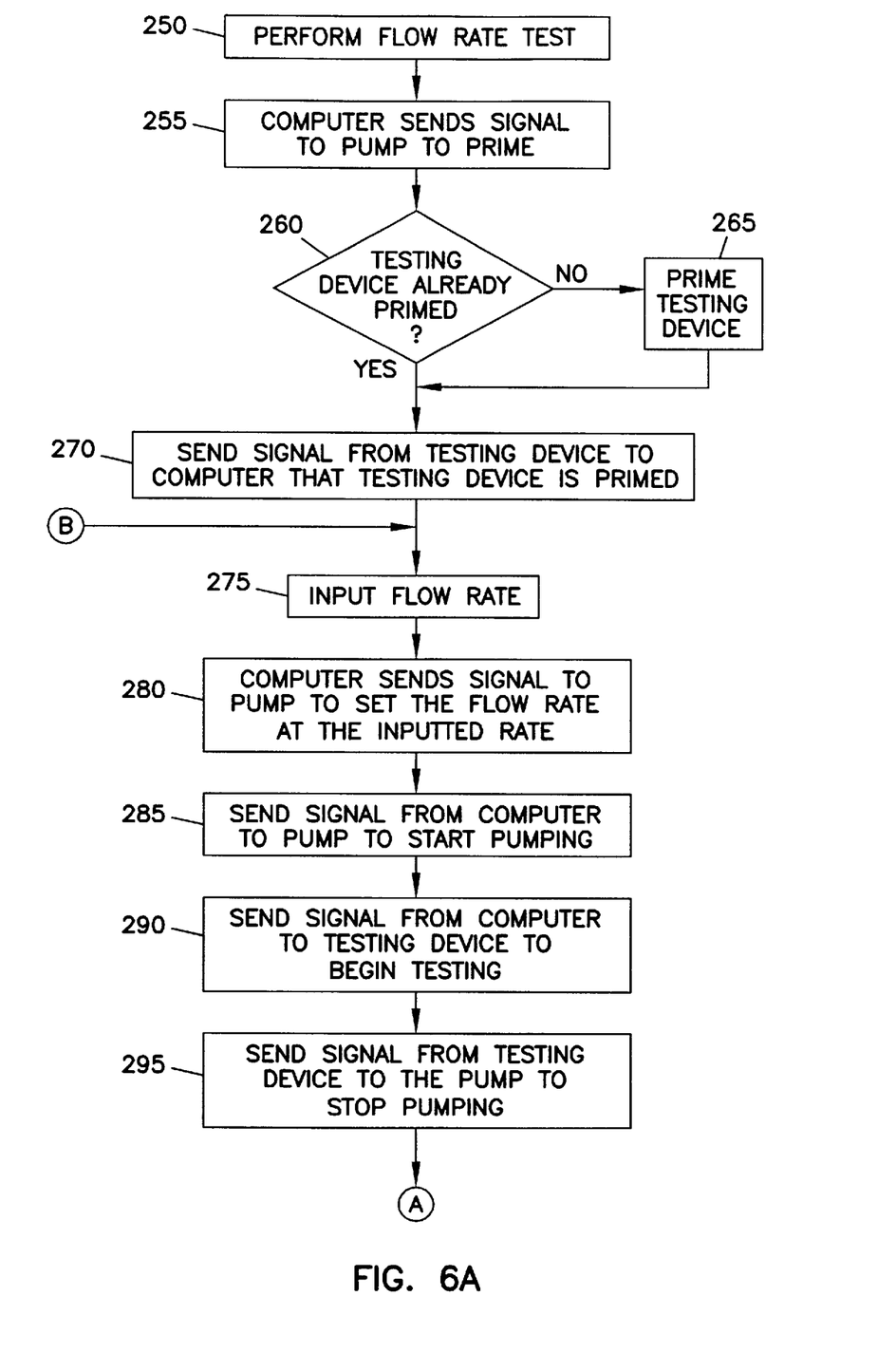
FIGS. 6A and 6B are flow chart representations of the preferred steps taken during the flow test identified in the flow chart of FIG. 4.
Figure 6B:
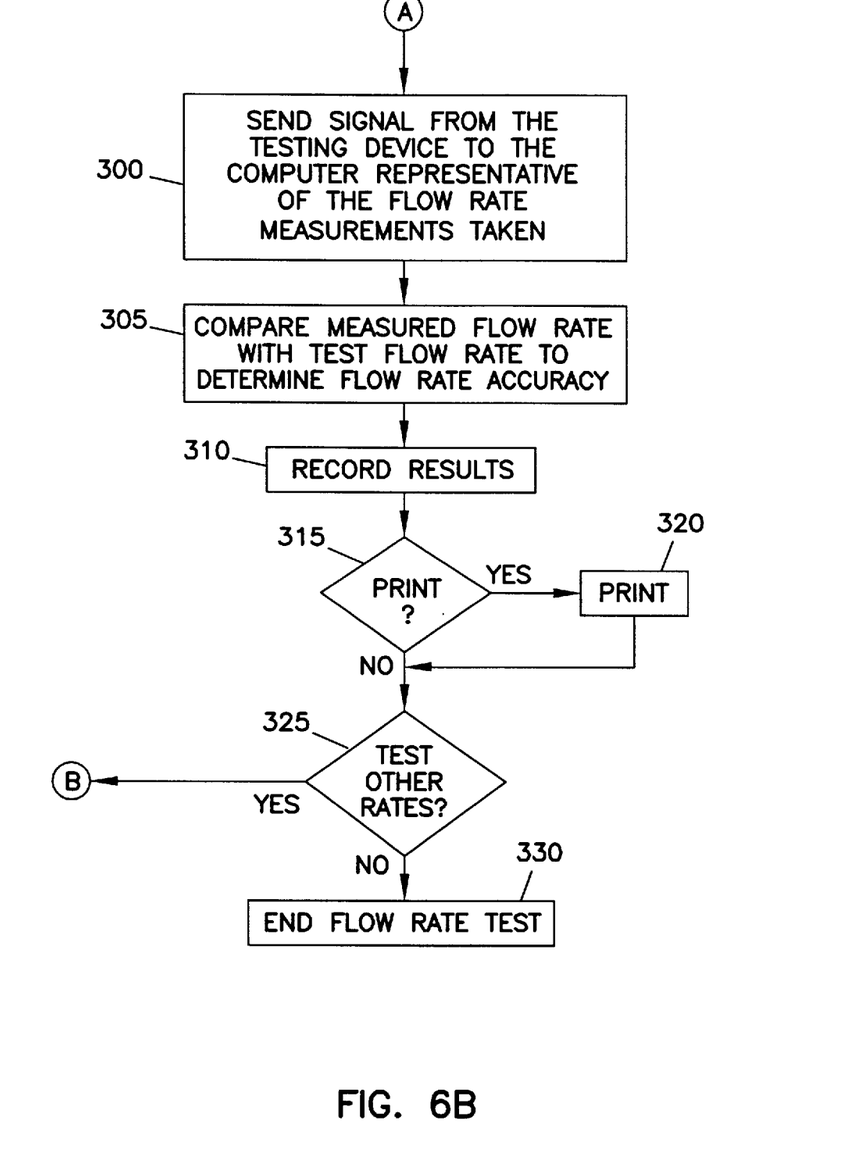

FIGS. 6A and 6B illustrate a flow chart representation of steps in a preferred flow rate test. In order to perform this test, system 10 must be primed. Accordingly, at 255, computer 11 sends a signal to pump 12 instructing it to start priming the system. At 260, a check is made to determine whether testing device 13 is already primed. If not, at 265, computer 11 sends a signal to pump 12 to prime the testing device. If so, at 270, testing device 13 sends a signal back to computer 11 indicating that the testing device is primed.

At 275, computer 11 instructs the operator to input a test flow rate. Computer 11 may be programmed to provide the operator with a menu listing a variety of commonly tested flow rates from which to choose. In a preferred embodiment, computer 11 may automatically command pump 12 to test the flow rate at a single test flow rate or at several test flow rates, such as in a range from a low flow rate to a high flow rate. At 280, computer 11 sends a signal to pump 12 setting the pump at the flow rate chosen by the operator. At 285, computer 11 sends a signal to pump 12 to start pumping. At 290, computer 11 sends a signal to flow rate tester 44 of testing device 13 to begin the flow rate test. After a predetermined period of time, at 295, testing device 13 sends a signal via computer 11 to pump 12 to stop pumping. If the flow rate is automatically selected, steps 275, 280, and 285 are not necessary.

At 300, testing device 13 sends a signal to computer 11 representative of the flow rate measurements taken by the testing device. Such measurements may include the duration of the test, instantaneous and average flow rate, and cumulative volume. It should be appreciated that signals representing real time test data can be sent to computer 11 anytime throughout the duration of the test, provided the infusion is continuous.

At 305, computer 11 compares the measured flow rate with the test flow rate to determine flow rate accuracy. At 310, computer 11 records the test results. At 315, a check is made whether to print the test results. If so, at 320 the results are printed to printer 41. If not, at 325, a check is made whether other flow rates should be tested. If so, computer 11 repeats steps 275 through 320 until all desired testing is complete. Alternatively, the flow rate test results can be printed at the conclusion of all the test procedures (see FIG. 4). Once all flow rate testing is complete, at 330, the flow rate test is ended.

Figure 7:
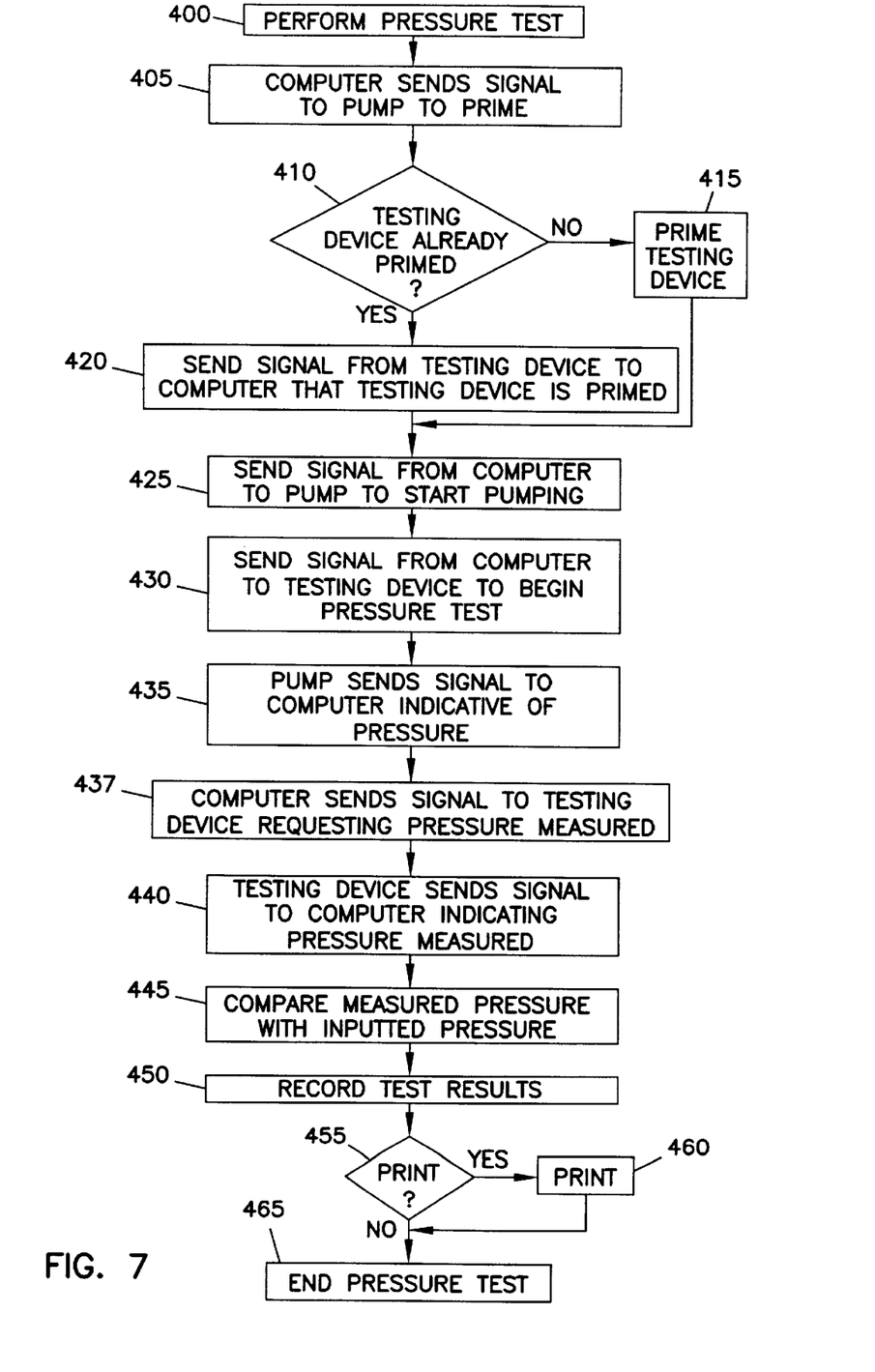
FIG. 7 is a flow chart representation of the preferred steps taken during the pressure test identified in the flow chart of FIG. 4.

FIG. 7 illustrates a flow chart representation of steps taken in a preferred pressure test. As with flow rate tester 44, system 10 must be primed in order to perform this test. Accordingly, at 405, computer 11 sends a signal to pump 12 instructing it to start priming. At 410, a check is made to determine whether testing device 13 is already primed. If not, at 415, computer 11 sends a signal to testing device 13 to prime the testing device. If so, at 420, testing device 13 sends a signal back to computer 11 indicating that the testing device is primed.

At 425, computer 11 sends a signal to pump 12 to start pumping. At 430, computer 11 sends a signal to pressure tester 46 of testing device 13 to begin the pressure test. Pump 12 is set to stop pumping due to an occlusion in tube 15 when the pressure of pump 12 reaches a predetermined level due to the activation of pressure sensor 24 at a predetermined pressure sensed by sensor 24. As previously mentioned, pump 12 may also be set to pump to test one or more pre-selected test pressure settings below the predetermined level where pumping will cease.

At 435, once pump 12 has stopped pumping or has reached the predetermined pressure or pre-selected test pressure, pump 12 sends a signal to computer 11 representative of the pressure sensed by pressure sensor 24. At 437, computer 11 sends a signal to testing device 13 requesting the pressure measured by the testing device. At 440, testing device 13 sends a signal to computer 11 representative of the pressure measured. It should be appreciated, however, that signals representing real time test data can be sent to computer 11 anytime throughout the duration of pressure test 46.

At 445, computer 11 compares the pressure measured by testing device 13 with the pressure received from pump 12 to determine the accuracy of the response of pump 12 to the occlusion in tube 15 and the accuracy of pressure sensor 24. In an alternate but less desirable mode of operation, the operator himself or herself can read the measured pressure and compare it to the pressure of pump 12 to determine pressure accuracy.

At 450, computer 11 records the tests results. At 455, a check is made whether to print the test results. Alternatively, the pressure test results can be printed at the conclusion of all test procedures (see FIG. 4). If so, at 460, the results are printed to printer 41. If not, at 465, pressure test 46 is ended.

Figure 8A:
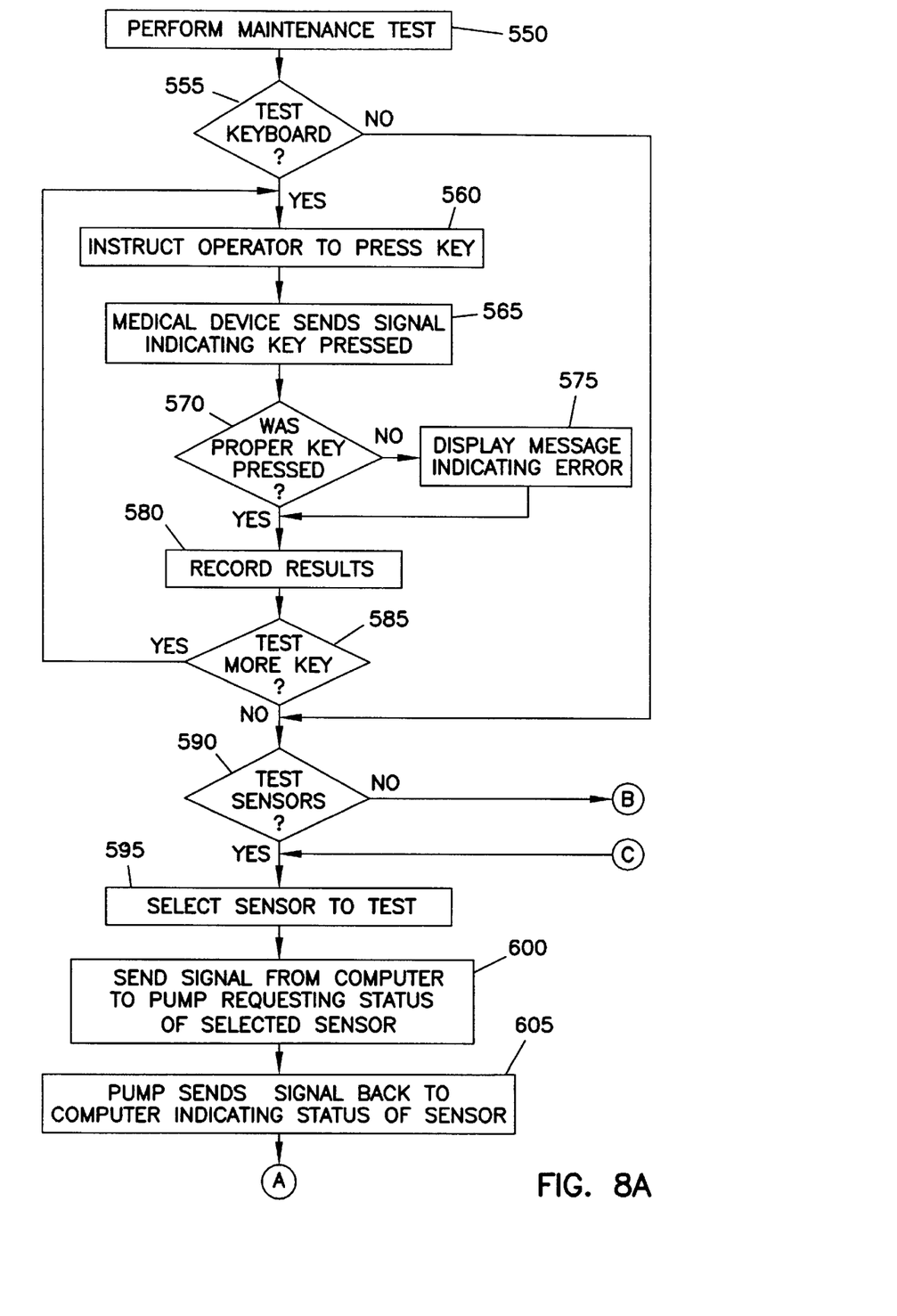
FIGS. 8A and 8B are flow chart representations of the preferred steps taken during the maintenance test identified in the flow chart of FIG. 4.
Figure 8B:
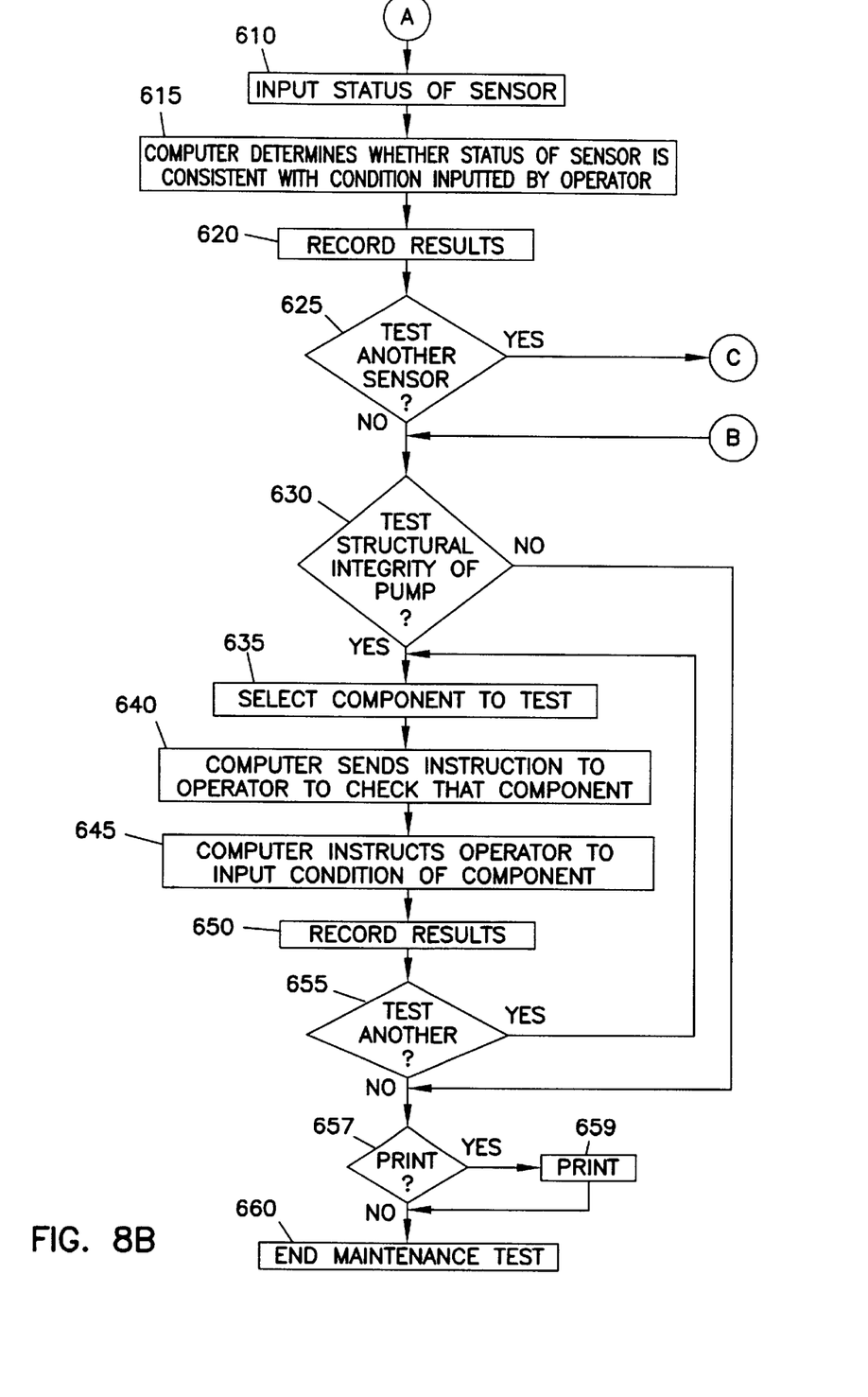

FIGS. 8A and 8B illustrate a flow chart representative of steps taken during a preferred maintenance test 550. At 555, a check is made to determine whether the keyboard (input structure 18) of pump 12 should be tested. If so, at 560, computer 11 sends a signal to the operator to press a key. At 565, pump 12 sends a signal back to computer 11 indicating which key was pressed. At 570, a check is made to determine whether the key pressed is the same as the key being tested. If not, at 575, a message is displayed on monitor 39 of computer 11 indicating the error. At 580, computer 11 records the results. At 585, a check is made to determine whether to test more keys. If so, steps 560 through 580 are repeated until all the desired keys have been tested.

If no more keys are to be tested, at 590, a check is made to determine whether to test any of the sensors of pump 12. If so, at 595, computer 11 instructs the operator to select the sensor to be tested. At 600, computer 11 sends a signal to pump 12 requesting the status of that sensor. At 605, pump 12 sends a signal back to computer 11 indicating the status of the sensor. At 610, computer 11 instructs the operator to input the status of the sensor being tested. At 615, computer 11 determines whether the status of the sensor is consistent with the condition inputted by the operator.

Computer 11 could instruct the operator to change the status of the sensor. For example, if the latch on the cassette door was closed, the operator could be instructed to unlatch the cassette door. Computer 11 could then determine whether the status of the sensor changed accordingly.

At 620, computer 11 records the results. At 625, a check is made to determine whether the operator wishes to test another sensor. If so, steps 595 through 620 are repeated until all the desired sensors have been tested.

If no more sensors are to be tested, at 630, a check is made to determine whether to test the structural integrity of pump 12. If so, at 635, computer 11 instructs the operator to input the name of the component to be tested. Alternatively, computer 11 could be programmed to provide the operator with a menu from which to chose which components to test. At 640, computer 11 instructs the operator to inspect the component selected. This inspection may be visual and/or physical. At 645, computer 11 instructs the operator to input the condition of the component. Alternatively, computer 11 could be programmed to provide the user with a rating system from which to rate the component's condition. Such ratings, for example, could include: broken, damaged but operable, fair, etc. At 650, computer 11 records the result. At 655, a check is made to determine whether another component should be tested. If so, steps 635 through 650 are repeated until all desired components are tested. At 657, a check is made to determine whether to print the test results. Alternatively, the maintenance test results can be printed at the conclusion of all test procedures (see FIG. 4). If so, at 659, the results are printed to printer 41. If not, at 660, maintenance test 48 is ended.

In a preferred embodiment, computer 11 is also preferably programmed to provide the operator with other instructions relating to the particular component being tested, such as how to clean it, how to repair it, if possible, and other related instructions.

The foregoing constitutes a description of various features of a preferred embodiment. Numerous changes to the preferred embodiment are possible without departing from the spirit and scope of the invention. Hence, the scope of the invention should be determined with reference not to the preferred embodiment, but to the following claims.

What is claimed is:

1. A pump comprising:

a tube;

a pumping mechanism engaged with the tube; and a control system for controlling operation of the pumping mechanism, the control system including:

a communications port;

a processor connected to the communications port; and a memory connected to the processor, the memory including first program means for communicating with an external computer system through the communications port via signals sent to and from the processor of the control system, and second program means for conducting a test of the pump when the processor is communicating with the external computer system.

* * * * *